United States Patent [19]

Stricker

[11] 4,409,206
[45] Oct. 11, 1983

[54] TRANSDERMAL RELEASE SYSTEM FOR PHARMACEUTICAL PREPARATION

[75] Inventor: Herbert Stricker, Stettiner, Fed. Rep. of Germany

[73] Assignee: Boehringer Ingelheim GmbH, Ingelheim am Rhein, Fed. Rep. of Germany

[21] Appl. No.: 292,882

[22] Filed: Aug. 14, 1981

Related U.S. Application Data

[63] Continuation of Ser. No. 145,839, May 1, 1980, abandoned.

[30] Foreign Application Priority Data

May 21, 1979 [DE] Fed. Rep. of Germany ....... 2920500

[51] Int. Cl.³ .................. A61K 31/78; A61K 9/70; A61L 15/03
[52] U.S. Cl. ......................................... 424/81; 424/28
[58] Field of Search ................................. 424/81, 28

[56] References Cited

U.S. PATENT DOCUMENTS 3,598,123  8/1971  Zaffaroni .................. 424/20

*Primary Examiner*—Albert T. Meyers
*Assistant Examiner*—John W. Rollins
*Attorney, Agent, or Firm*—Hammond & Littell, Weissenberger and Muserlian

[57] ABSTRACT

This invention is directed to a pharmaceutical preparation for transdermal application, which comprises a film comprising a skin-compatible polyacrylate, which swells in water and a pharmaceutically active substance in amorphous form.

The invention is also directed to the preparation of said pharmaceutical preparation and its use in administering pharmaceutically active substances.

24 Claims, 7 Drawing Figures

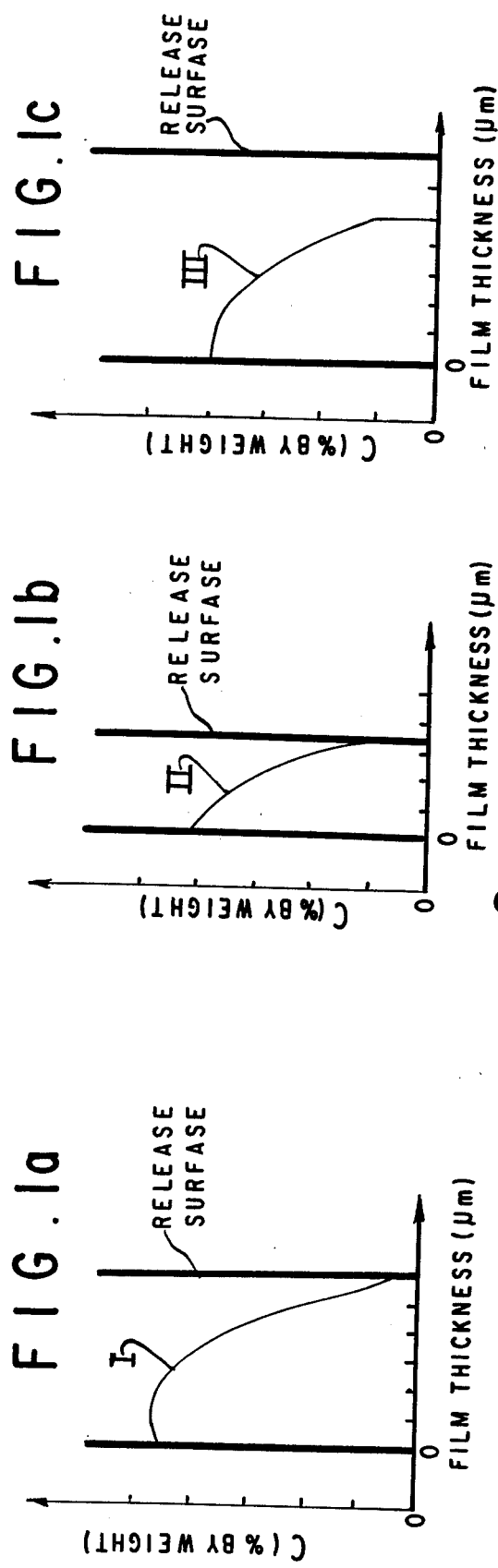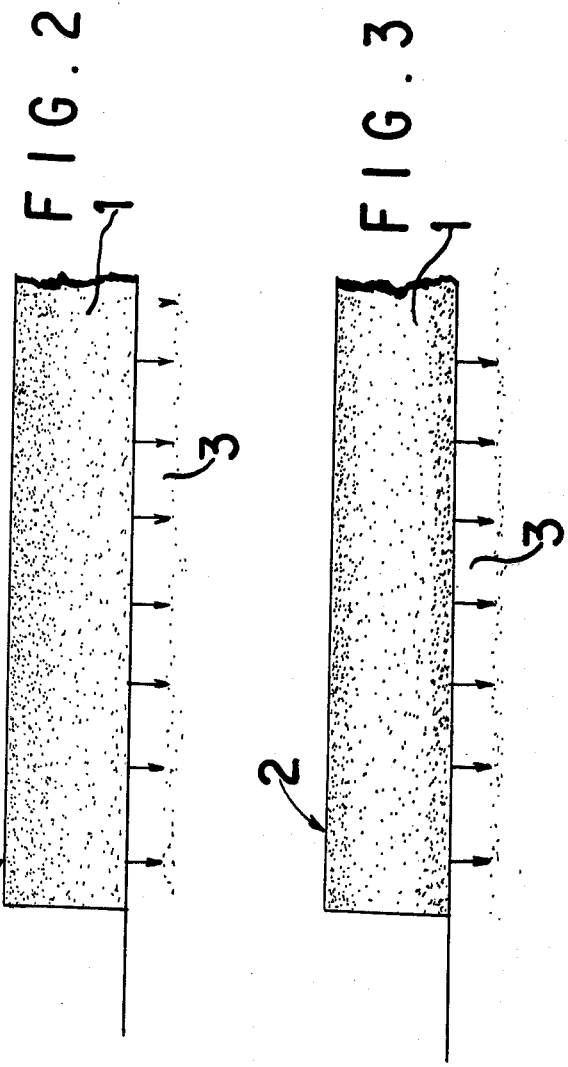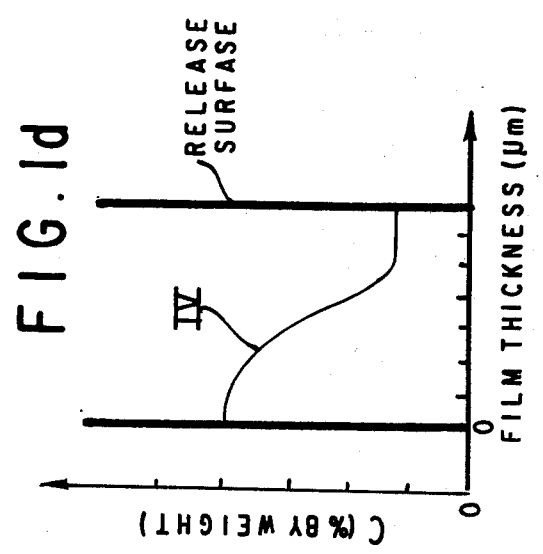

TRANSDERMAL RELEASE SYSTEM FOR PHARMACEUTICAL PREPARATION

CROSS-REFERENCE TO RELATED APPLICATION

This application is a continuation of co-pending U.S. patent application Ser. No. 145,839, filed May 1, 1980 abandoned.

FIELD OF THE INVENTION

The invention relates to a transdermal release for pharmaceuticals. More particularly, the release system comprises a polyacrylate film preparation which is suitable for transdermal long-term therapy with systemic drugs.

BACKGROUND OF THE INVENTION

Many drugs are capable of penetrating the skin and getting into the general circulation system where they act systemically. Drugs which can be given in low doses and whose penetration is so great that the rate of invasion into the general circulation system can be controlled over the rate at which the active substance is released from the preparation, can be administered over longer periods of time more reliably and more accurately by means of a transdermal form of administration than, for example, per os. The advantages of the introduction of drugs into the general circulation system through the skin are the elimination of uncontrollable factors of gastrointestinal resorption, the reduction of the metabolism by avoiding the first liver passage, and the effects which are generally desired in retard forms, such as avoidance of high initial blood level concentrations and attainment of a constant blood level over a long period of time.

Various transdermal release systems for systemic drugs are known. U.S. Pat. Nos. 3,598,122, 3,598,123, 3,742,951, 3,787,494, 3,998,934, 3,995,632, 4,060,084, 3,731,683, and 4,031,894 describe sandwich-type or laminar bandages and adhesive plasters which consists of a supporting frame forming one surface of the bandage, a reservoir containing the systemic drug in solid suspended form, means applied on the surface of the reservoir for regulating the rate of release, as well as means for fastening the bandage or plaster on the skin. In addition, substrates in foil form with incorporated active substances are known from German Published Applications (DE-OS) Nos. 24 32 925, 22 18 200, and 22 07 635, which substrates consist of hydroxyalkyl cellulose, polyamino acids, or the like. Due to their complicated structure, the multi-layered systems are difficult to produce and require high investment and manufacturing costs. In addition, the effective substance contained in suspended form in multi-layered systems is only utilized to a limited extend, which corresponds to a low bio-availability. The other polymeric substrates consist of substances which are soluble in water and are therefore not suitable for dermal long-term application.

OBJECTS OF THE INVENTION

It is an object of this invention to provide a novel transdermal release system for pharmaceuticals.

It is also an object of the invention to avoid the disadvantages of the prior art and to provide a pharmaceutical delivery means in the form of a film which is simple and inexpensive to produce, which ensures a reproducible, controlled release with low temperature-dependence and a constant rate up to high dosage, and which permits variation of the rate of release within wide limits.

It is a further object of the invention to provide a pharmaceutical preparation comprising skin-compatible polyacrylate and pharmaceutical in amorphous form.

These and other objects of the invention will become more apparent in the discussion below.

BRIEF DESCRIPTION OF THE DRAWINGS

FIGS. 1a to 1d represent graphic profiles of active concentration versus film thickness in films according to the invention.

FIGS. 2 and 3 represent cross-sectional views of films according to the invention.

DETAILED DESCRIPTION OF THE INVENTION

Figure 4:
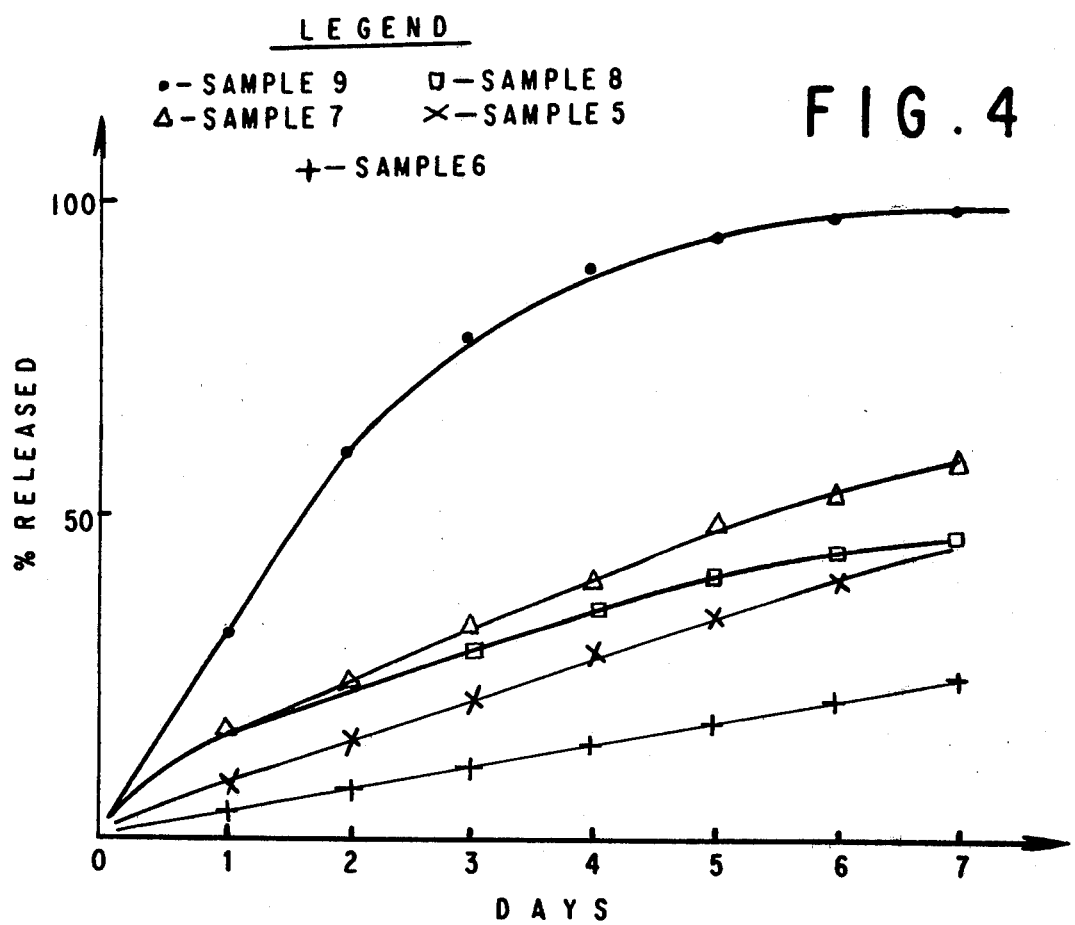
FIGS. 4 to 7 set forth the rates of release of different active substances according to the invention.

The invention herein relates to a pharmaceutical preparation in the form of a film wherein the film comprises a skin-compatible polyacrylate which swells in water, and wherein a pharmaceutical is embedded in amorphous form with a certain profile. The pharmaceutical preparation is intended to be affixed to, or placed next to, the skin of the person or animal to be treated.

The useful polyacrylate material, i.e., acrylic resin, comprises polymers or copolymers of acrylic acid and or methacrylic acid, alkyl esters thereof, and acrylonitrile. Preferably the alkyl radicals, which can be linear or branched, have from about 1 to 18 carbon atoms. The polyacrylate film is formed from a polyacrylate dispersion or suspension which comprises from about 20 to 90% by weight, preferably from about 30 to 80% by weight, of water or a suitable solvent, such as acetone, methylene chloride, etc.

A particularly suitable starting material for the production of the film is an aqueous dispersion of the polyacrylate, such as Eudargit ® E 30 D or Plex ® 4791 D, commercially available from Roehm, Darmstadt.

The polyacrylate dispersion or suspension can also contain hydrophilic auxiliary substance, such as, for example, polyethylene glycol, glycerin, sorbitol, or a mixture thereof, or the like, to regulate the rate of release of the pharmaceutical. The auxiliary substance can be present in an amount of from about 0 to 30 percent by weight, based on the weight of the polyacrylate. Suitable auxiliary substances include polyethylene glycol 400, i.e. polyethylene glycol having an average molecular weight of about 400, and Karion F ®, a sorbitol-containing composition available from Merck.

Preferably the pharmaceutical is in the form of a solid solution in the substrate. Dependent upon the type of active substance and the manufacturing conditions, a solid suspension of the amorphous pharmaceutical can also be obtained. It has previously been known to attempt to reduce the gradual decrease in the rate of release, which is caused by the increasing diffusion layer thickness, by employing a deposit of a solid drug and a saturated solution in the film matrix. According to the invention, however, the increasing diffusion layer thickness is compensated by a corresponding concentration profile of the active substance, as shown in FIGS. 1a to 1d, so that the rate of release remains practically constant up to relatively high rates of release. The profile is substantially characterized in that the concentration of the active substance in the polymer film rises with increasing distance from the release surface.

The pharmaceutical preparation according to the invention is produced by dissolving desired auxiliary substances in the desired amount of aqueous polyacrylate dispersion and then pouring the dispersion onto a flat, contained surface. The dispersion is allowed to dry, possibly at elevated temperature, such as from about 30°–80° C. The desired pharmaceutical subsequently is applied to the dry polyacrylate film in the form of an organic solution or suspension, such as, for example, in an ethanol, ethanol-water, or methylene chloride solution or in suspension in a fluorocarbon such as Freon ® or water, after which the solvent is evaporated.

To vary the concentration profile of the active substance over the film cross-section, the pharmaceutical dispersion can be applied once or several times on either or both sides of the polyacrylate film. This represents, after appropriate packaging, the finished pharmaceutical preparation in the sense of the invention, which preparation is charged with the active substance. In situations where polyacrylate dispersion or suspension is also subsequently applied, the subsequently applied polyacrylate forms a bond with the base, i.e., the initial polyacrylate film, in such as way that a completely homogeneous film is obtained.

The rate of release of a pharmaceutical from the pharmaceutical preparation of this invention is dependent upon the polyacrylate employed. It is also particularly dependent upon the following:

(a) the conditions under which the polyacrylate film is charged with active substace, i.e., type or amount of solvent, temperature, etc.;
(b) film thickness; and
(c) the type and amount of water-binding auxiliary substances added to the polyacrylate dispersion. The concentration profile of a pharmaceutical, determinant for the size and course of the state of release, is influenced by the above factors in various ways. In FIGS. 1a to 1d, several concentration profiles are set forth in terms of the concentration of pharmaceutical C (percent by weight) versus the film thickness. Exemplary of the effect of some of the factors discussed, it can be noted that with increasing drying temperature and decreasing film thickness, the profile of FIG. 1a, Profile I, is displaced toward the profile of FIG. 1b, Profile II. The profile of FIG. 1c, Profile III, represents the effect of water-binding auxiliary substances, such as polyethylene glycol 400, which lead, on the one hand, to an increase of the water-absorption of the film on the skin, and on the other hand, to a significant reduction of the temperature-dependence of the release of the active substance. FIG. 1d, i.e., Profile IV, represents a typical concentration profile for a relatively thick film.

FIGS. 2 and 3 set forth aspects of the invention in a form different from that of FIGS. 1a to 1d. FIGS. 2 and 3, which correspond to FIGS. 1a and 1d, respectively, are each a cross-sectional view of a film having a certain pharmaceutical concentration profile. In FIG. 2 it can be seen that the concentration of pharmaceutical 1 in the polyacrylage film 2 increases with distance from the skin 3. In FIG. 3, the pharmaceutical concentration 1 near the skin 3 is greater than in FIG. 2.

The pharmaceutical preparation of the invention can be used for the application of virtually any pharmaceutical suitable for topical administration. Useful pharmaceuticals include the following:

Antihypertonics, e.g., clonidine, i.e., clonidine hydrochloride; tranquilizers, e.g. haloperidol; coronary drugs, e.g., nitroglycerin; migraine drugs, e.g., dihydroergotamine; corticoids; contraconceptives; analgesics; antirheumatics; and anticholinergics.

The polyacrylate films containing the active substance can be applied on the skin with or without a special adhesive layer, since they already have by nature certain adhesive properties. Without a special adhesive layer, they can be fixed either by means of suitable adhesive plasters or, on the extremities, for example, by means of an elastic bandage. The adhesion of the film is greatly increased if the respective part of the skin is first moistened with ethanol. For the application of the adhesive layer, the latter is applied in the above-described manner on the drug-containing film, using, however, instead of polyacrylate a suitable acrylic resin dispersion, such as, for example, Plex 4853 D ®, available from Roehm.

The polyacrylate films can be any suitable size, shape, and/or thickness. However, the size and thickness of the films as well as the amounts of active substance present will depend upon the particular dosage of the particular pharmaceutical to be administered, as can be determined by one skilled in the art. A typical film may be a rectangle of from about 2 to 6 cm by from about 2 to 10 cm, or a differently shaped film having a surface area of from about 4 to 60 cm². The film thickness will be uniform and will be from about 10 to 500 μm, preferably from about 20 to 200 μm.

The primary advantage of the pharmaceutical preparation according to the invention is that a skin-compatible, physiologically harmless film-former is used in which the drug is distributed in amorphous form (mostly as a solid solution) with a certain profile. Also, the preparation can advantageously be produced in a simple and inexpensive manner without requiring much equipment since only small amounts of organic solvents are required. The preparation manifests a well-reproducible, controlled release that is at a constant rate up to high dosages and is only slightly temperature-dependent, so that great bio-availability is ensured. In addition, production can be adapted to various conditions and objectives, particularly since it is possible to set various rates of release.

The following examples are intended to illustrate the invention and should not be construed as limiting the invention thereto.

EXAMPLES

EXAMPLE 1

Clonidine-containing Preparation

An aqueous polyacrylate dispersion was poured under dust-free conditions onto a smooth, exactly plumbed surface (polypropylene plate). The drying of the dispersion was effected at 22° C. and 35% relative humidity. After the dispersion dried to a clear, transparent, blister-free film, a solution of clonidine was applied, and the solvent was removed completely by drying under the above-mentioned climatic conditions. Subsequently, the dispersion of clonidine was applied again and allowed to dry. After complete drying, a clear, transparent, homogeneous polyacrylate film was obtained. Auxiliary substances, if any, would have been added first to the polyacrylate dispersion. The composition of the components of different films with embedded clonidine is set forth in the following table:

TABLE I

Composition of Clonidine-Polyacrylate Films

| Sample | Solvent[7] | Active Substance Applied (% by wt. in solution) | (ml/cm$^2$) | Polyacrylate (mg/cm$^2$) |
|---|---|---|---|---|
| 1 | Methylene Chloride | 1.65 | 0.127 | 51.0[5] |
| 2 | Methylene Chloride | 1.65 | 0.127 | 51.0[3] |
| 3 | Methylene Chloride | 1.65 | 0.127 | 51.0[6] |
| 4 | Methylene Chloride | 1.65 | 0.127 | 51.0[4] |
| 5 | Ethanol | 3.3 | 0.0637 | 35.7[1] |
| 6 | Ethanol | 3.3 | 0.0637 | 35.7[2] |
| 7 | Ethanol | 3.3 | 0.0637 | 25.5 |
| 8 | Ethanol + H$_2$O (2:1) | 3.3 | 0.0637 | 35.7[2] |
| 9 | Ethanol | 3.3 | 0.0637 | 15.3 |

[1] of which 10.2 mg/cm$^2$ of polyacrylate plus 10% polyethylene glycol 400 were applied later.
[2] of which 10.2 mg/cm$^2$ of polyacrylate were applied later.
[3] of which 25.5 mg/cm$^2$ of polyacrylate were applied later.
[4] of which 25.5 mg/cm$^2$ of polyacrylate plus 10% of Karion F were applied later.
[5] of which 25.5 mg/cm$^2$ of polyacrylate plus 25% polyethylene glycol 400 were applied later.
[6] of which 25.5 mg/cm$^2$ of polyacrylate plus 10% glycerin were applied later.
[7] for clonidine

EXAMPLE 2

Nitroglycerin-containing Preparation

A film comprised of 25.5 mg/cm$^2$ of polyacrylate was prepared from a 30% aqueous dispersion according to the procedure of Example 1. The film was subsequently smoothed by treatment with methanol. Charging of the film with nitroglycerin (2.6 mg/cm$^2$) was effected by applying a 1% ethanol solution twice, drying each time for 24 hours. To obtain an optimum profile for the active substance, 15.3 mg/cm$^2$ of polyacrylate were applied to the top of the preparation by applying a 30% aqueous dispersion as described above.

EXAMPLE 3

Dihydroergotamin methane sulfone-containing Preparation

In accordance with the procedure of Example 1, a polyacrylate film (15.4 mg/cm$^2$) was charged with 2.4 mg/cm$^2$ of active substance in the form of either (a) a 2% methanolchloroform-solution or (b) a 2% methanol solution.

EXAMPLE 4

Haloperidol-methane-sulfone-containing Preparation

In accordance with the procedure described in Example 1, a polyacrylate film (19.8 mg/cm$^2$) was produced and charged with 6.15 mg/cm$^2$ of active substance in the form of a methanol-chloroform-solution. After drying, 8.1 mg/cm$^2$ of polyacrylate were applied to one surface of the film.

Properties of Polymeric Films Containing Active Substances

To determine the in-vitro release rates of active substance, pieces of films prepared according to the examples above and having surface areas of about 5 cm$^2$, which pieces were covered on the back, were placed in 10 ml of demineralized water at 33° C., which solution was stirred slightly, changed daily, and analyzed to determine the rates of release of the active substances.

The results of the analyses are set forth in FIGS. 4 to 7 and the tables below.

FIG. 4 depicts the release of clonidine from polyacrylate films as a function of time. A comparison of Samples 6, 7, and 9 from Example 1 shows to what extent the release depends on the profile of the active substance over the film cross-section. A comparison of Samples 6 and 8 and Samples 5 and 6 illustrates beyond that the effect of the solvent and/or of the water-binding auxiliary substances (such as polyethylene glycol 400).

Figure 5:
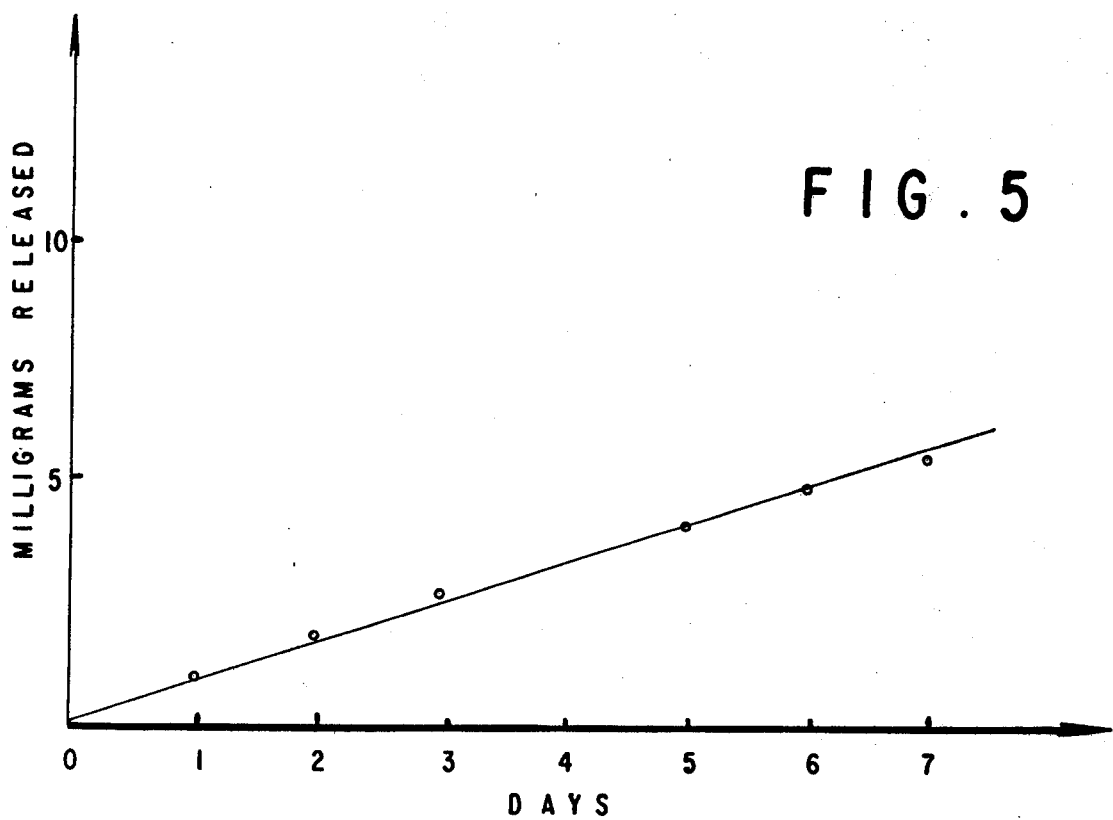
Figure 6:
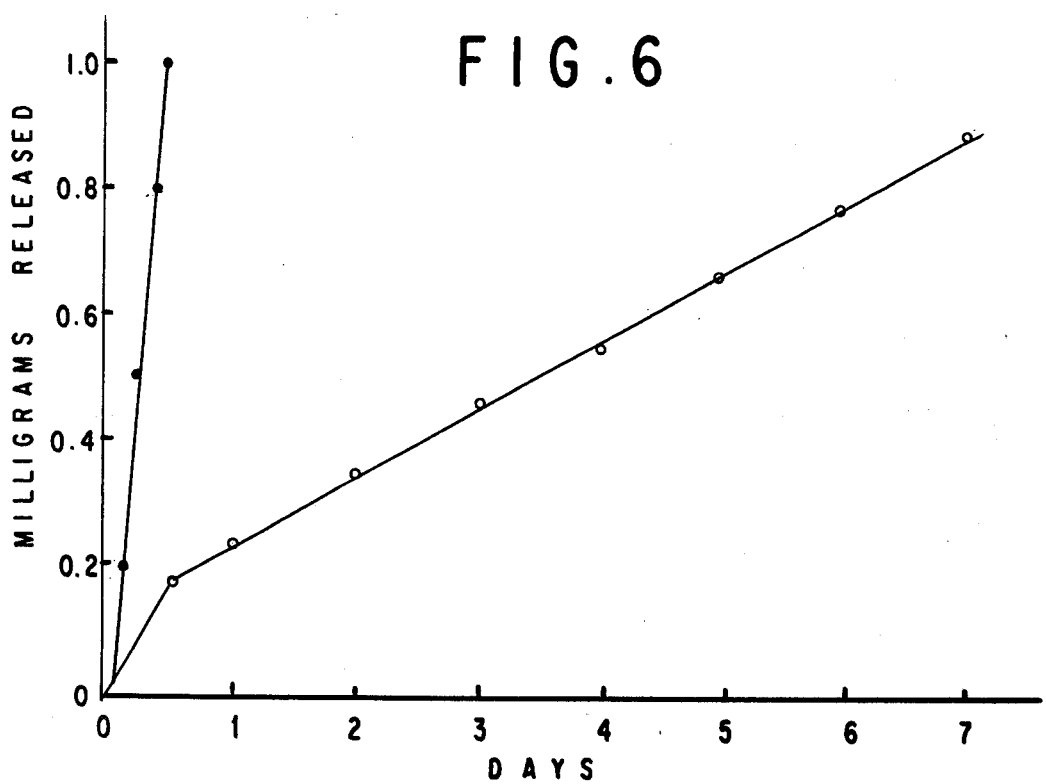
Figure 7:
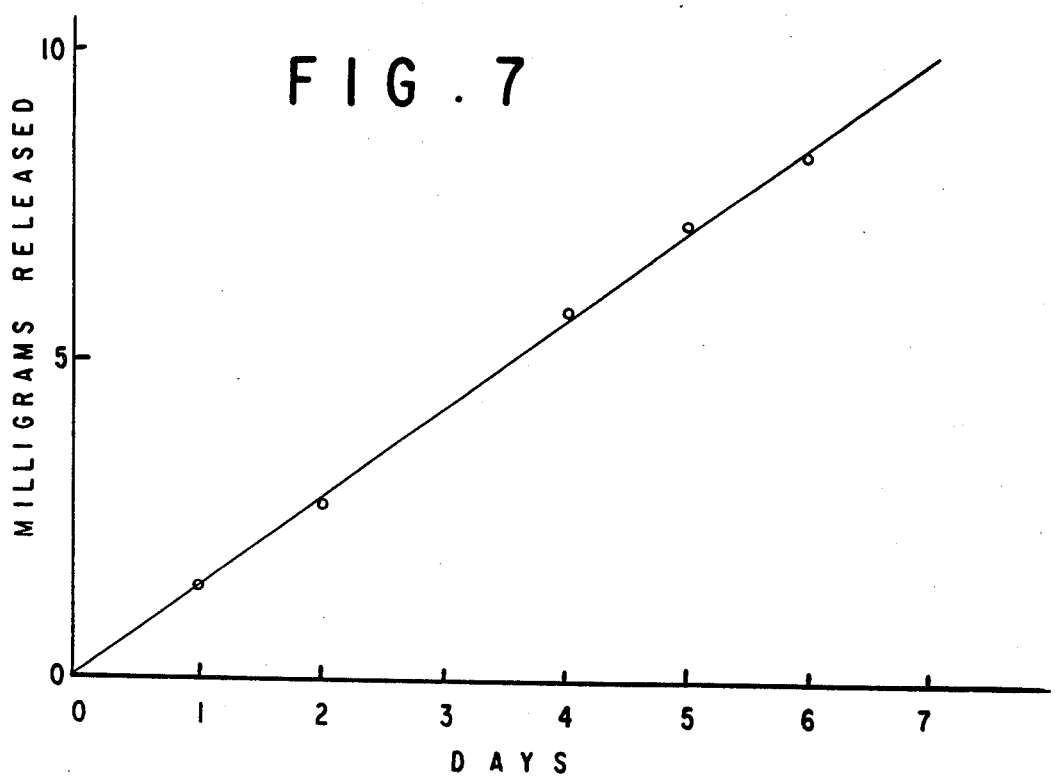

FIGS. 5 to 7 set forth the release characteristics of the polyacrylate films containing the active substances described in Examples 2, 3, and 4.

The temperature-dependence of the release of the active substance is of great importance for a constant dosage. The table below contains data which show that polyacrylate films, such as Sample 6 of Example 1, for example, are slightly temperature-dependent in their release behavior in the range of from 25°–35° C.

TABLE II

Temperature-dependence of the In-Vitro Release of Clonidine from Polyacrylate Films

| Temperature | Percent Released | | |
|---|---|---|---|
| | First Day | Second Day | Third Day |
| 25° C. | 7.0 | 6.0 | 6.0 |
| 33° C. | 8.0 | 6.5 | 6.5 |

The adsorption and desorption behavior of the polyacrylate films is an important factor for the stability and biopharmaceutical quality. The water absorption of the films at 99% relative humidity is greatly increased, by, for example, polyethylene glycol 400, glycerin, and sorbitol, as is set forth in the following table:

TABLE III

Adsorption and Desorption Isotherms of Polyacrylate Films

| Sample[3] | Auxiliary Substance | Adsorption[1] % H$_2$O 2 Hrs. | % H$_2$O max. 7 Days | Desorption[2] % H$_2$O 2 Hrs. | % H$_2$O max. 2 Days |
|---|---|---|---|---|---|
| 2 | — | 1.1 | 15 | 4.0 | 15 |
| 3 | 9% glycerin | 2.6 | 50 | 5.0 | 50 |
| 4 | 9% Karion F | 5.0 | 40 | 6.0 | 40 |
| 1 | 25% polyethylene glycol 400 | 4.2 | 70 | 10.0 | 70 |

[1] 99% relative humidity, 37° C. subsequently
[2] 40% relative humidity 23° C.
[3] From Example 1

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A method for preparing a pharmaceutical preparation for transdermal application which comprises the steps of:
 (a) pouring unto a flat, contained surface a polyacrylate dispersion or suspension comprising (i) from about 10 to 80% by weight of skin-compatible polyacrylate material selected from the group consisting of polymers or co-polymers of acrylic acid, methacrylic acid, acrylic acid and methacrylic acid, alkyl esters thereof, and acrylonitrile, (ii) from about 20 to 90% by weight of water or a suitable solvent, and (iii) from 0 to about 30% by weight of hydrophilic substance selected from the group consisting of polyethylene glycol, glycerin, sorbitol, and mixtures thereof;
(b) allowing the water or organic solvent to evaporate from the polyacrylate dispersion or suspension of step (a) to form a dry polyacrylate film;
(c) contacting one or both surfaces of the polyacrylate film from step (b) one or more times with an organic solution or suspension of a pharmaceutically active substance selected from the group consisting of antihypertonics, tranquilizers, coronary drugs, migraine drugs, corticoids, contraceptives, analgesics, antirheumatics, and anticholinergics; and
(d) allowing the organic solvent or suspension agent to evaporate from the polyacrylate film of step (c) to form a polyacrylate film comprising pharmaceutically active substance in amorphous form, the resulting polyacrylate film having a thickness of from about 10 to 500 μm.

2. A method for preparing a pharmaceutical preparation for transdermal application which comprises the steps of:
(a) pouring unto a flat, contained surface a polyacrylate dispersion or suspension comprising (i) from about 10 to 80% by weight of skin-compatible polyacrylate material selected from the group consisting of polymers or co-polymers of acrylic acid, methacrylic acid, acrylic acid and methacrylic acid, alkyl esters thereof, and acrylonitrile, (ii) from about 20 to 90% by weight of water, acetone, or methylene chloride, and (iii) from 0 to about 30% by weight of hydrophilic substance selected from the group consisting of polyethylene glycol, glycerin, sorbitol, and mixtures thereof;
(b) allowing the water, acetone, methylene chloride to evaporate from the polyacrylate dispersion or suspension of step (a) to form a dry polyacrylate film;
(c) contacting one or both surfaces of the polyacrylate film from step (b) one or more times with a pharmaceutically active substance selected from the group consisting of clonidine, haloperidol, nitroglycerin, and dihydroergotamine in solution in ethanol, a mixture of ethanol and water, or methylene chloride or in suspension in a fluorocarbon or water; and
(d) allowing the organic solvent or suspension agent to evaporate from the polyacrylate film of step (c) to form a polyacrylate film comprising pharmaceutically active substance in amorphous form, the resulting polyacrylate film having a thickness of from about 10 to 500 μm.

3. The method of claim 2, wherein the polyacrylate dispersion or suspension in step (a) is an aqueous dispersion.

4. The method of claim 2, wherein step (b) takes place at a temperature of from about 30° to 80° C.

5. The method of claim 2, wherein the pharmaceutically active substance is clonidine.

6. The method of claim 2, wherein in an additional step a polyacrylate dispersion is poured onto the polyacrylate film from step (d) and the polyacrylate film is allowed to dry.

7. The method of claim 6, wherein the additional step is repeated one or more times.

8. The method of claim 1, wherein the polyacrylate dispersion or suspension in step (a) contains from about 20 to 70% by weight of polyacrylate material.

9. The method of claim 1, wherein the polyacrylate dispersion or suspension in step (a) is an aqueous dispersion.

10. The method of claim 1, wherein the polyacrylate suspension in step (a) contains acetone or methylene chloride.

11. The method of claim 1, wherein step (b) takes place at a temperature of from about 30° to 80° C.

12. The method of claim 1, wherein in step (c) the pharmaceutically active substance is in solution in ethanol, a mixture of ethanol and water, or methylene chloride.

13. The method of claim 1, wherein in step (c) the pharmaceutically active substance is in suspension in a fluorocarbon or water.

14. The method of claim 1, wherein in step (c) the pharmaceutically active substance in an antihypertonic, tranquilizer, coronary drug, or migraine drug.

15. The method of claim 14, wherein the pharmaceutically active substance is clonidine, haloperidol, nitroglycerin, or dihydroergotamine.

16. The method of claim 15, wherein the pharmaceutically active substance is clonidine.

17. The method of claim 1, wherein in an additional step a polyacrylate dispersion is poured onto the polyacrylate film from step (d) and the polyacrylate dispersion is allowed to dry.

18. The method of claim 17, wherein the additional step is repeated one or more times.

19. A pharmaceutical preparation for transdermal application prepared according to claim 1.

20. The pharmaceutical preparation of claim 19, which has a surface area on one side of from about 4 to 60 cm².

21. The pharmaceutical preparation of claim 19, which is a rectangle of from about 2 to 6 cm by from about 2 to 10 cm.

22. The pharmaceutical preparation of claim 19, wherein the film thickness is from about 20 to 200 μm.

23. A method of administering a pharmaceutically active substance to a warm-blooded animal which comprises maintaining the skin of said animal in contact with the pharmaceutical preparation of claim 19.

24. The method of claim 23, wherein the skin is moistened with ethanol prior to initially contacting the skin with the pharmaceutical preparation.

* * * * *

UNITED STATES PATENT AND TRADEMARK OFFICE
CERTIFICATE OF CORRECTION

PATENT NO. : 4,409,206
DATED     : October 11, 1983
INVENTOR(S) : HERBERT STRICKER It is certified that error appears in the above-identified patent and that said Letters Patent is hereby corrected as shown below:

Column 1, line 56:  "extend" should read -- extent --.

Column 8, line 2 of Claim 14:  "in" should read -- is --.

Signed and Sealed this

Twenty-sixth Day of March 1985

[SEAL]

Attest:

DONALD J. QUIGG

*Attesting Officer*   *Acting Commissioner of Patents and Trademarks*